United States Patent [19]

Ohba et al.

[11] Patent Number: 5,037,993

[45] Date of Patent: Aug. 6, 1991

[54] SULFONYL DERIVATIVES OF AN ANTIBIOTIC SUBSTANCE ISOLATED FROM STREPTOMYCES

[75] Inventors: Kazunori Ohba; Masaji Sezaki; Shinichi Kondo; Masao Koyama; Tadashi Nakazawa; Haruo Yamamoto, all of Kanagawa, Japan

[73] Assignee: Meiji Seika Kaisha Ltd., Tokyo, Japan

[21] Appl. No.: 520,424

[22] Filed: May 8, 1990

Related U.S. Application Data

[60] Division of Ser. No. 344,738, Apr. 28, 1989, Pat. No. 4,994,578, and a continuation-in-part of Ser. No. 276,714, Nov. 28, 1988, abandoned.

[30] Foreign Application Priority Data

Nov. 27, 1987 [JP] Japan .................................. 62-297476
Apr. 19, 1988 [JP] Japan .................................. 63-94544
Apr. 28, 1988 [JP] Japan .................................. 63-103782

[51] Int. Cl.$^5$ ............................................ C07D 487/04
[52] U.S. Cl. .................................................. 548/433
[58] Field of Search ........................................ 548/433

[56] References Cited

FOREIGN PATENT DOCUMENTS 0154445  9/1985  European Pat. Off. .
0351865  1/1990  European Pat. Off. .
8706265 10/1987  Int'l Pat. Institute .

OTHER PUBLICATIONS

Yasuzawa et al., *Chemical and Pharmaceutical Bulletin*, 36:3728-3731 (1988).
Ohba et al., *The Journal of Antibiotics*, 41:1515-1519 (1988).

*Primary Examiner*—Mary C. Lee
*Assistant Examiner*—Michael G. Ambrose
*Attorney, Agent, or Firm*—Sughrue, Mion, Zinn, Macpeak & Seas

[57] ABSTRACT

Novel substances exhibiting antimicrobial activity and antitumor activity, a process for producing them by cultivating a microorganism belonging to the genus Streptomyces and capable of producing them and derivatives of such substances.

4 Claims, 12 Drawing Sheets

SULFONYL DERIVATIVES OF AN ANTIBIOTIC SUBSTANCE ISOLATED FROM STREPTOMYCES

This is a division of copending U.S. application Ser. No. 344,738, filed 4/28/89, now U.S. Pat. No. 4,994,578, which is a continuation-in-part of co-pending U.S Ser. No. 07/276,714 filed on Nov. 28, 1988 now abandoned, which is incorporated herein by reference.

FIELD OF THE INVENTION

This invention relates to novel antibiotics and to a process for preparing these antimicrobial substances. More particularly, it relates to novel antibiotics (hereinafter designated as SF2582 A, B, and C) which exhibit antitumor activity, to a process for preparing them by cultivation of a microorganism belonging to the genus Streptomyces and to derivatives of the antibiotics.

BACKGROUND OF THE INVENTION

A known compound which is similar to the antibiotic substances according to the present invention in physiochemical properties is CC-1065 as reported in D. G. Martin et al., *J. Antibiotics*, Vol. 34, 1119–1125 (1981). The antibiotic substances according to the present invention have been confirmed to clearly differ from CC-1065 in physiochemical properties and thereby to be novel antimicrobial substances.

A number of antimicrobial and antitumor substances have hitherto been reported, and some of them have been put into practical use as antimicrobials or anticancer agents. However, there are many unsolved problems in their application to the field of chemotherapy.

SUMMARY OF THE INVENTION

One object of this invention is to provide novel and useful antimicrobial and anticancer substances.

Another object of this invention is to provide a process for preparing such substances from microorganisms.

The inventors have isolated a number of microorganisms from the soil and searched substances produced therefrom. As a result, they have found that a certain kind of microorganism is capable of producing antibiotics exhibiting strong antimicrobial and antitumor activities. Further investigations have proved that these antibiotics are novel substances and produce excellent treating effects on experimentally induced tumors in animals. The inventors have also synthesized a number of derivatives of the substance and have found that a sulfate or an alkyl-or arylsulfonate of the substance shows intense antitumor activity. The present invention has been completed based on these findings.

BRIEF DESCRIPTION OF THE ACCOMPANYING DRAWINGS

DETAILED DESCRIPTION OF THE INVENTION

SF2582 A, B, and C according to the present invention have the following physiochemical properties. [I] SF2582 A represented by the formula (A):

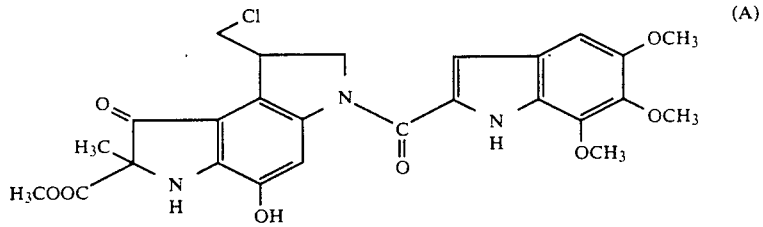

(1) Appearance: yellowish orange amorphous powder (2) Melting Point: 235°–237° C. (decomp.)

(3) Molecular Formula C$_{26}$H$_{26}$N$_3$O$_8$Cl [determined by high resolution mass spectrometry of a monoacetyl derivative; found: 585.1492; calcd. for C$_{28}$H$_{28}$N$_3$O$_9$Cl: 585.1512]

(4) Mass Spectrum:

SI-MS m/z 544 (M+1)$^+$

FD-MS m/s 543 (M)$^+$ (5) Specific Rotation: $[u]_D^{22}$ −51° (c=0.2, methanol)

Figure 1:
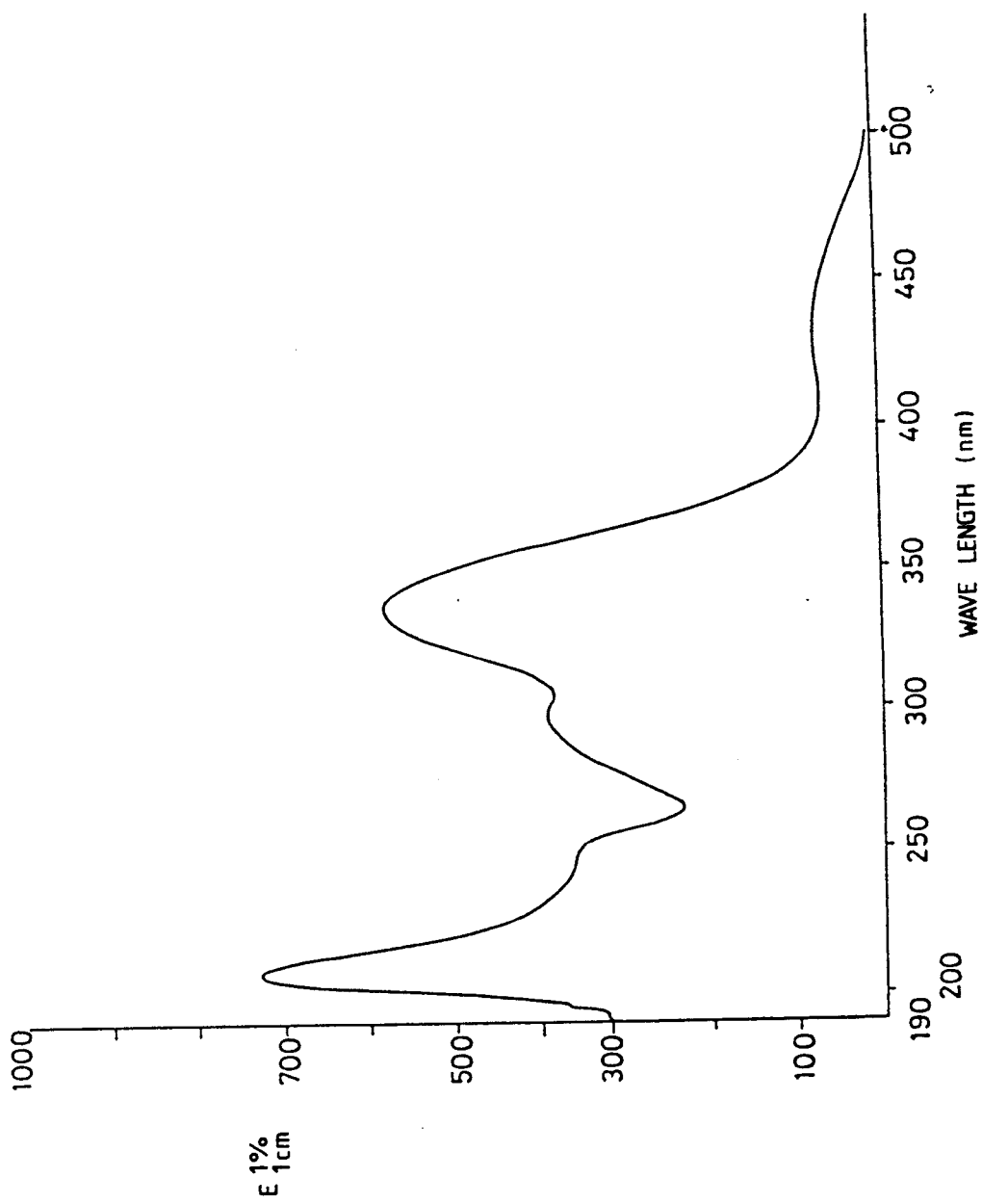
FIG. 1 shows a UV Spectrum of SF2582 A in a methanol solution.

(6) UV Spectrum: as shown in FIG. 1 $\delta_{max}$ (nm) (E$_{1cm}$1%) (in methanol solution): 208 (729), 245 shoulder (360), 298 (391), 337 (580), 432 (77)

Figure 2:
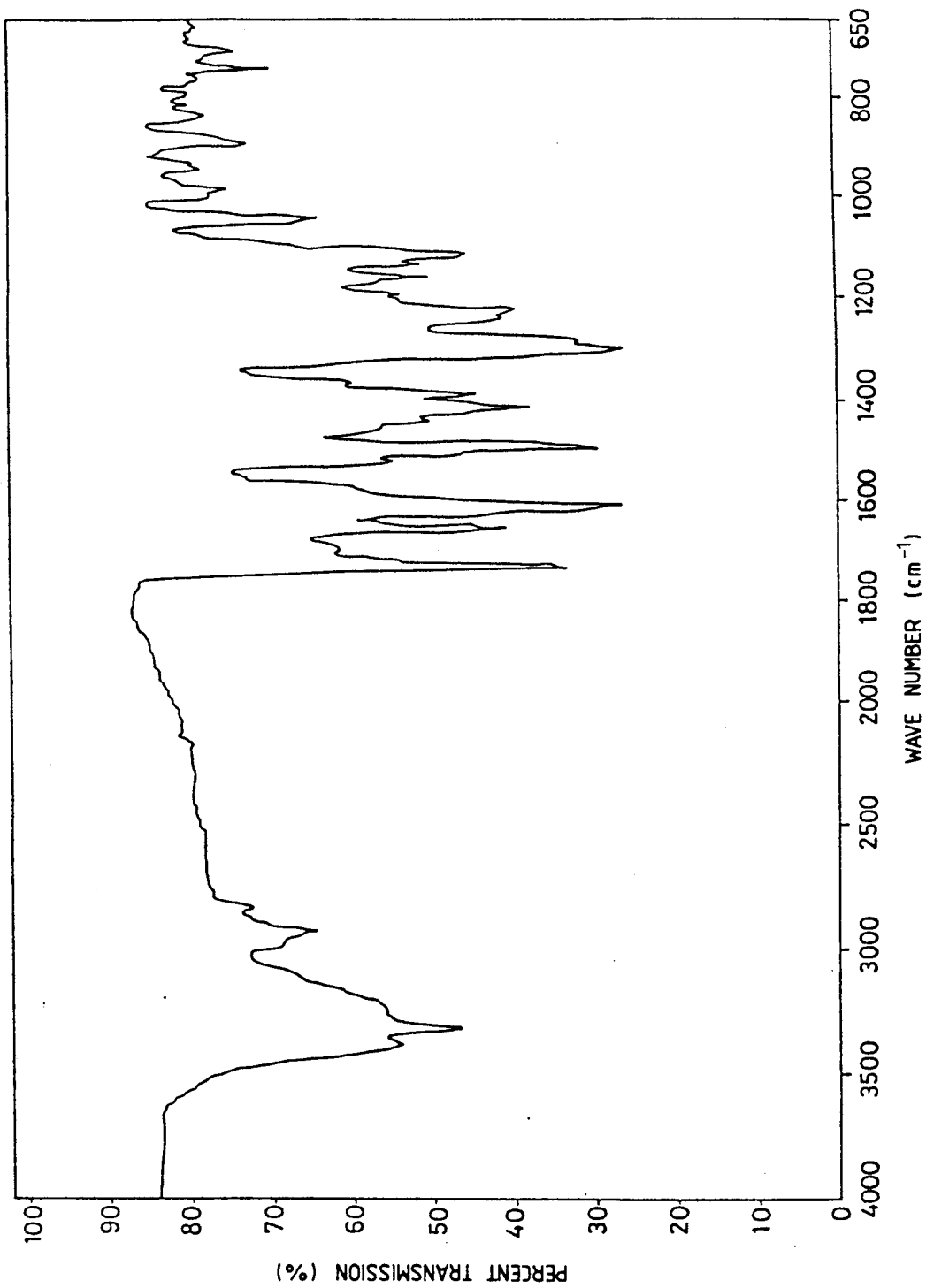
FIG. 2 shows an IR Spectrum of SF2582 A in a KBr tablet.

(7) IR Spectrum: as shown in FIG. 2

Figure 3:
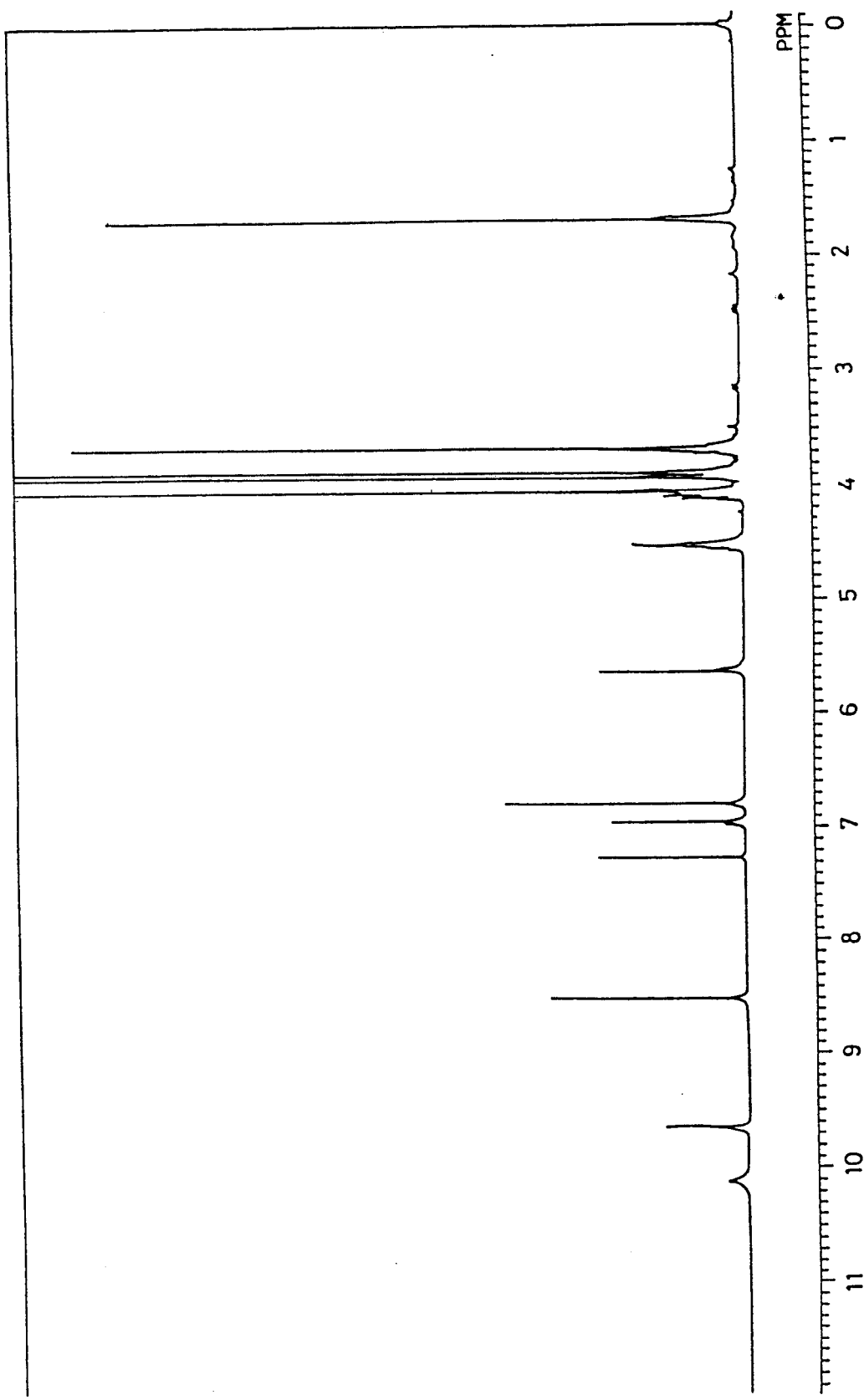
FIG. 3 shows a $^1$H NMR Spectrum (400 MHz) of SF2582 A in CDCl$_3$.

(8) $^1$H NMR Spectrum (400 MHz, CDCl$_3$): as shown in FIG. 3

Figure 4:
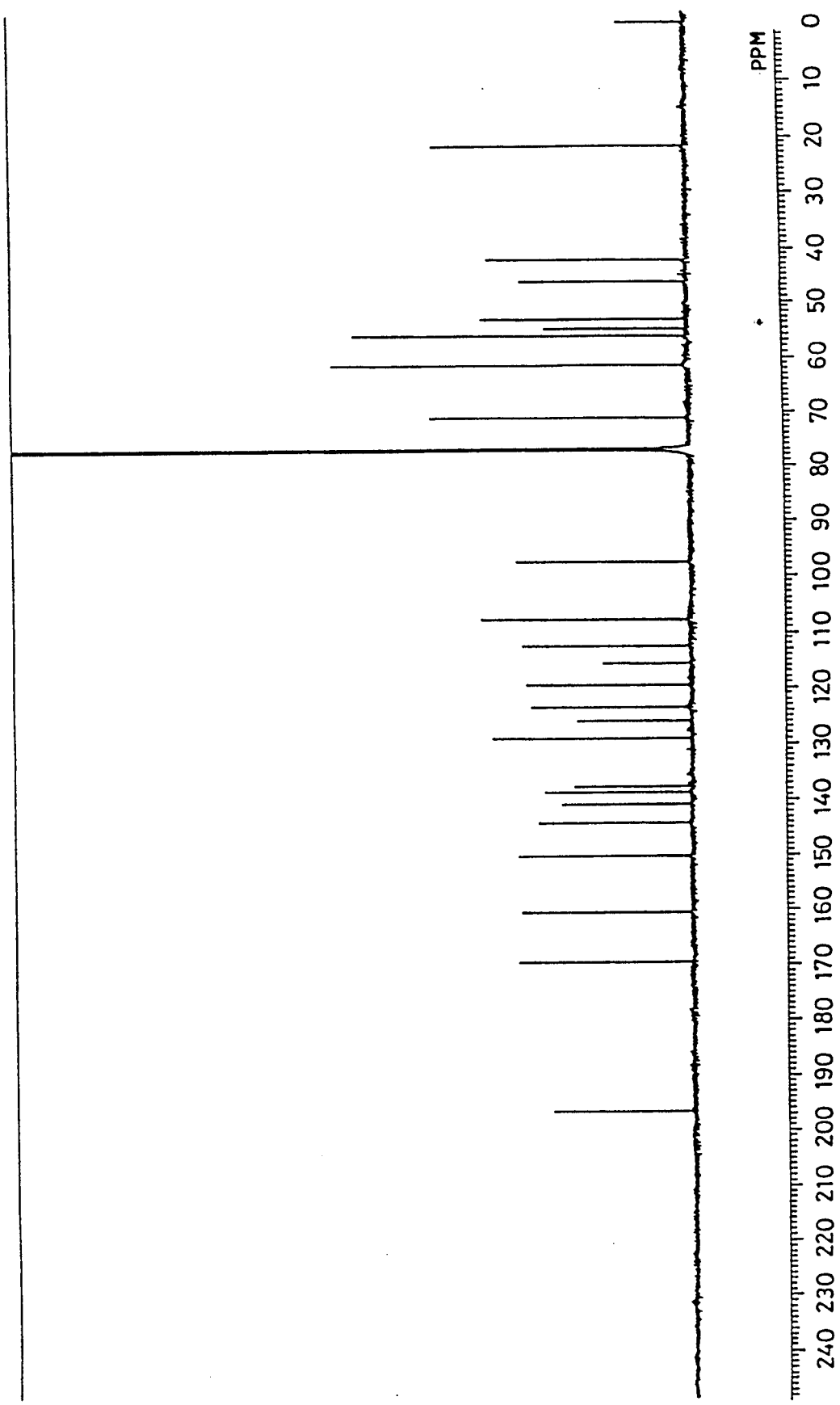
FIG. 4 shows a $^{13}$C NMR Spectrum (100 MHz) of SF2582 A in CDCl$_3$.

(9) $^{13}$C NMR Spectrum (100 MHz, CDCl$_3$) as shown in FIG. 4 δ (ppm): 196.6 (s), 169.5 (s), 160.5 (s), 150.2 (s), 150.1 (s), 144.1 (s), 140.7 (s), 138.6 (s), 137.6 (s), 129.0 (s), 125.9 (s), 123.4 (s), 119.5 (s), 115.5 (d), 112.4 (s), 107.8 (d), 97.7 (d), 71.1 (s), 61.5 (q), 61.2 (q), 56.3 (q), 54.9 (t), 53.3 (q), 46.3 (t), 42.2 (d), 21.9 (q)

(10) Solubility: soluble in methanol, ethyl acetate, acetone, chloroform, or dimethyl sufoxide; insoluble in water or haxane

(11) Thin Layer Chromatography (on silica gel plates produced by E. Merck, Darmstadt):

| Developing Solvent | Rf |
|---|---|
| chloroform-methanol (20:1) | 0.52 |
| benzene-acetone (2:1) | 0.48 |
| toluene-acetone (2:1) | 0.45 |

(12) Color Reaction: positive with 10% sulfuric acid reagent, Lemieux reagent, Greig-Leaback reagent, and molybdate-sulfuric acid reagent; negative with ninhydrin reagent

[II] SF2582 B:
represented by the formula (B):

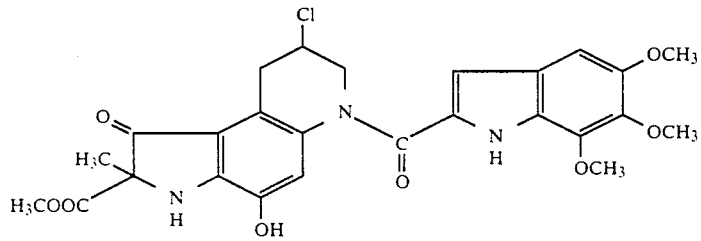

(1) Appearance: yellowish orange amorphous powder (2) Melting Point: 173°–175° C. (decomp.)

3) Molecular Formula: $C_{26}H_{26}N_3O_8Cl$ [determined by high resolution mass spectrometry of a monoacetyl derivative; found: 585.1519; calcd. for $C_{28}H_{28}N_3O_9Cl$: 585.1512]

(4) Mass Spectrum:

SI-MS 544 $(M+1)^+$

EI-MS 543 $(M)^+$ (5) Specific Rotation: $[u]_D^{22}$ −128° (c=0.2, methanol)

Figure 5:
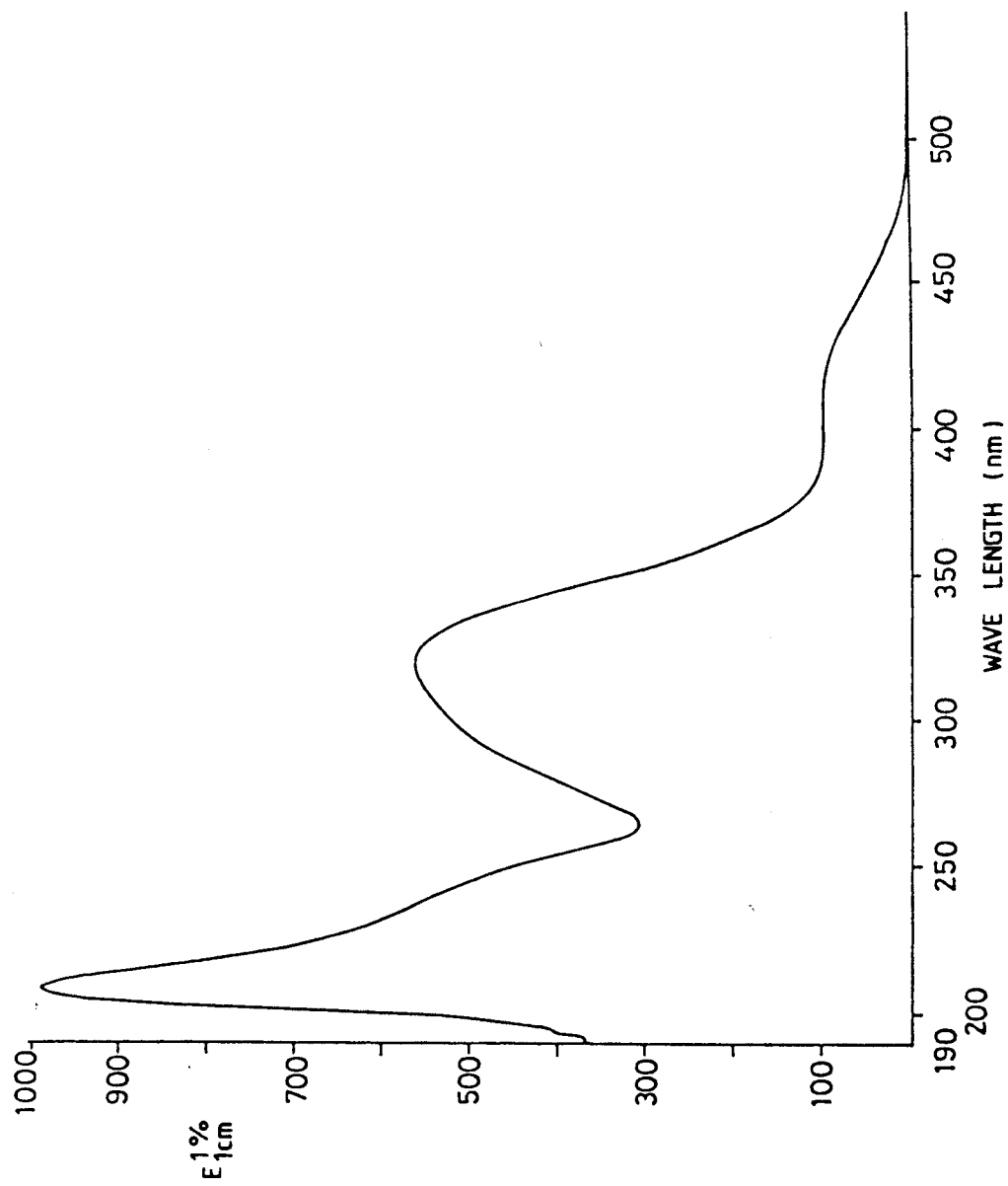
FIG. 5 shows a UV Spectrum of SF2582 B in a methanol solution.

(6) UV Spectrum: as shown in FIG. 5 $\delta_{max}$ (nm) ($E_{1cm}^{1\%}$) (in methanol solution): 210 (991), 320 (563), 400–410 (99)

Figure 6:
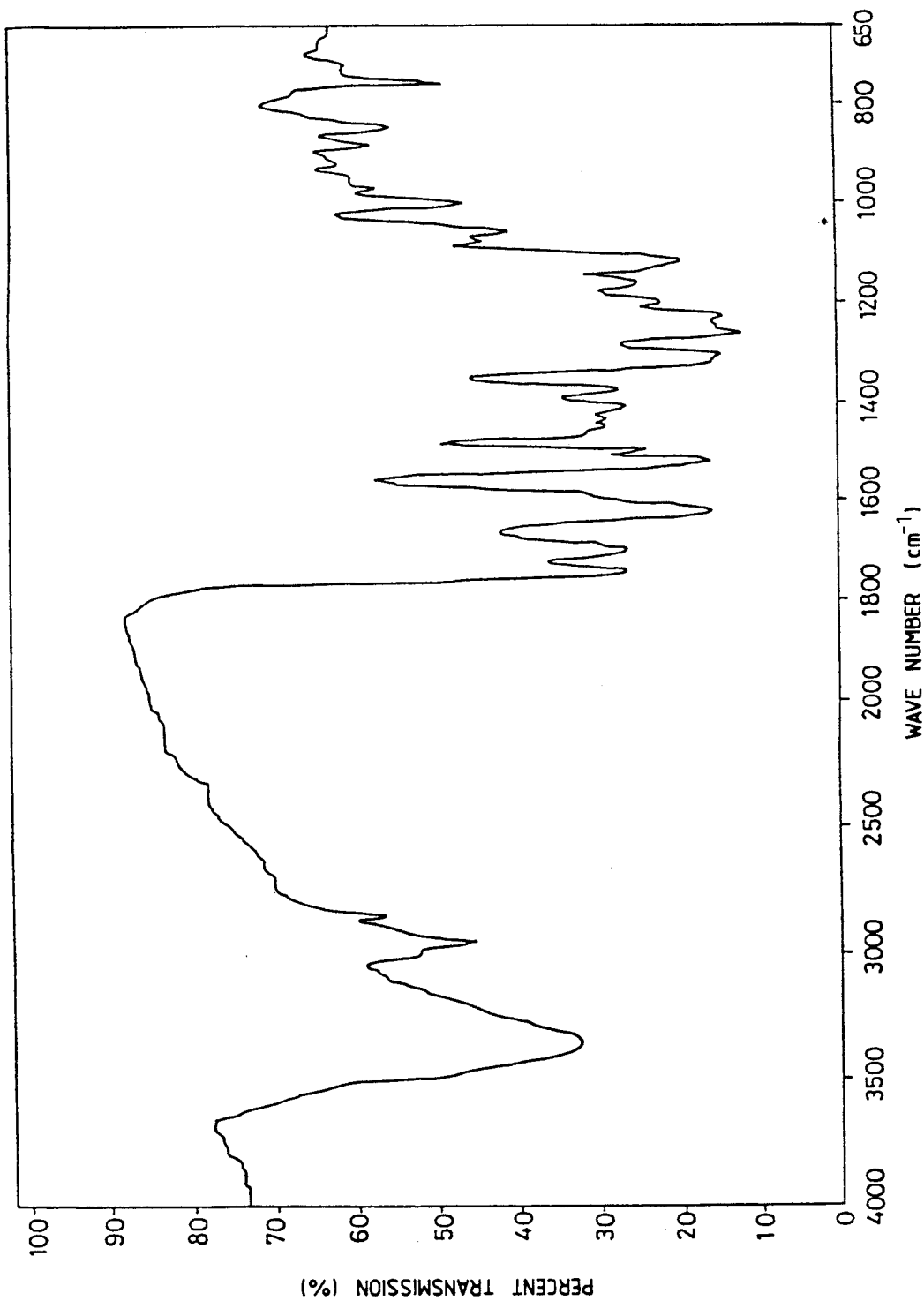
FIG. 6 shows an IR Spectrum of SF2582 B in a KBr tablet.

(7) IR Spectrum: as shown in FIG. 6

Figure 7:
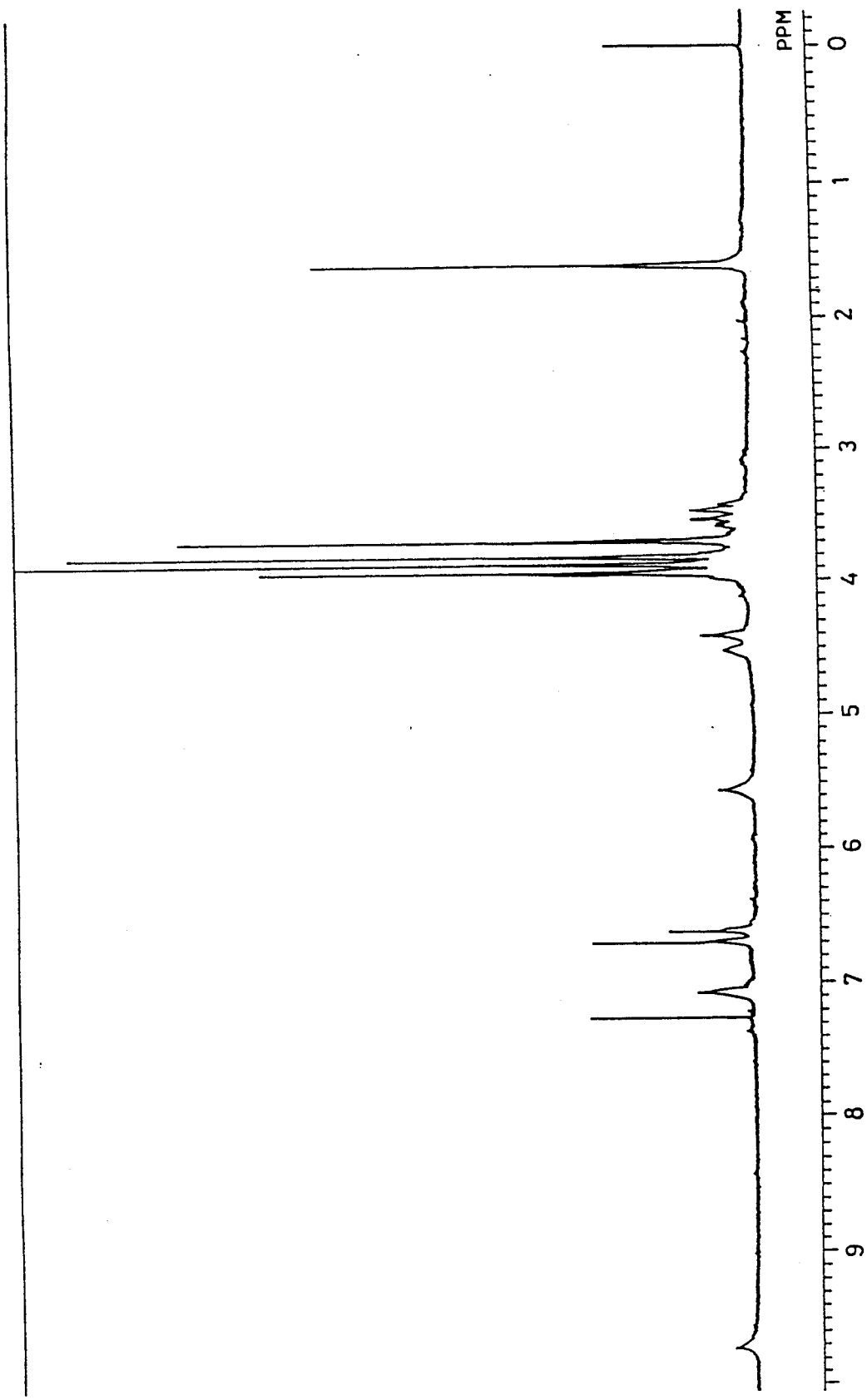
FIG. 7 shows a $^1$H NMR Spectrum (400 MHz) of SF2582 B in CDCl$_3$.

(8) $^1$H NMR Spectrum (400 MHz, CDCl$_3$): as shown in FIG. 7

Figure 8:
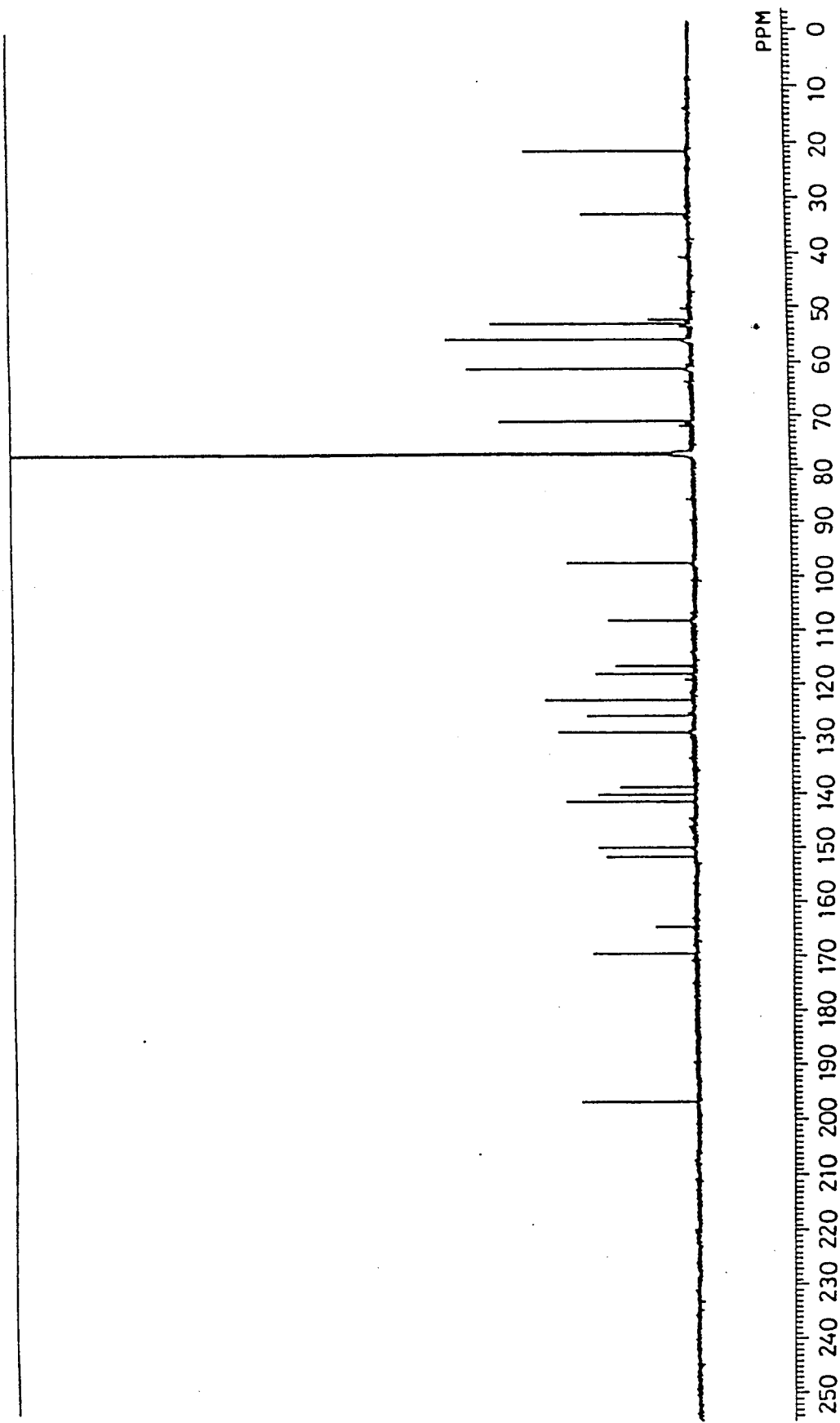
FIG. 8 shows a 13C NMR Spectrum (100 MHz) of SF2582 B in CDCl$_3$.

(9) $^{13}$C NMR Spectrum (100 MHz, CDCl$_3$): as shown in FIG. 8 δ(ppm): 196.8 (s), 169.6 (s), 164.7 (s), 151.6 (s), 150.0 (s), 141.6 (s), 140.2 (s), 138.8 (s), 129.1 (s), 128.8 (s), 125.9 (s), 123.0 (s), 118.0 (d), 116.7 (s), 116.6 (s), 108.1 (d), 97.6 (d), 71.0 (s), 61.4 (q), 61.1 (q), 56.2 (q), 53.6 (d), 53.4 (q), 52.5 (t), 33.1 (t), 21.8 (q)

(10) Solubility: soluble in methanol, ethyl acetate, acetone, chloroform, or dimethyl sufoxide; insoluble in water or hexane

(11) Thin Layer Chromatography (on silica gel plates produced by E. Merck, Darmstadt):

| Developing Solvent | Rf |
|---|---|
| chloroform-methanol (20:1) | 0.50 |
| benzene-acetone (2:1) | 0.45 |
| toluene-acetone (2:1) | 0.44 |

(13) Color Reaction: positive with 10% sulfuric acid reagent, Lemieux reagent, Greig-Leaback reagent, and molybdate-sulfuric acid reagent; negative with ninhydrin reagent

[III] SF2582 C:
represented by the formula (C)

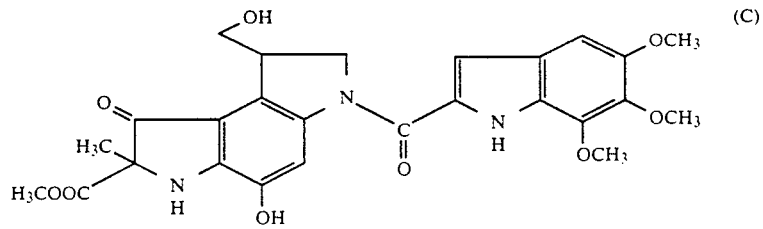

(1) Appearance: orange crystalline powder (2) Melting Point: >240° C.

(3) Elementary Analysis: C 59.24%, H 5.12%, N 7.98%

(4) Molecular Formula: $C_{26}H_{27}N_3O_9$ (5) Mass Spectrum EI-MS m/z 525 $(M^+)$ (6) Specific Rotation: $[\alpha]_D^{22}$ −54° (c=0.1, methanol)

Figure 9:
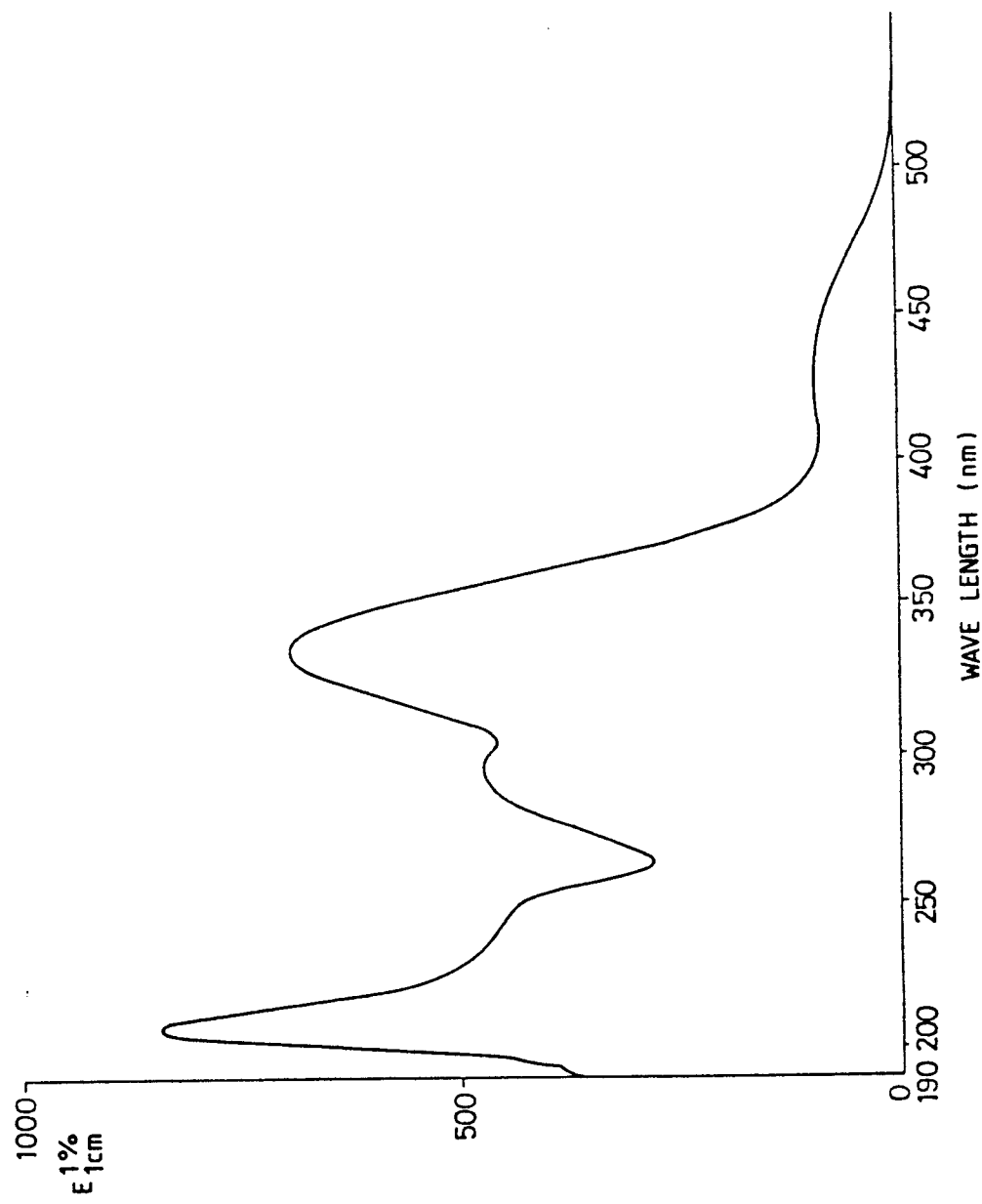
FIG. 9 shows a UV Spectrum of SF2582 C in a methanol solution.

(7) UV Spectrum: as shown in FIG. 9 $\delta_{max}$ (nm) ($E_{1cm}^{1\%}$) (in methanol solution): 208 (845), 245 shoulder (450), 297 (473), 336 (690), 432 (93)

Figure 10:
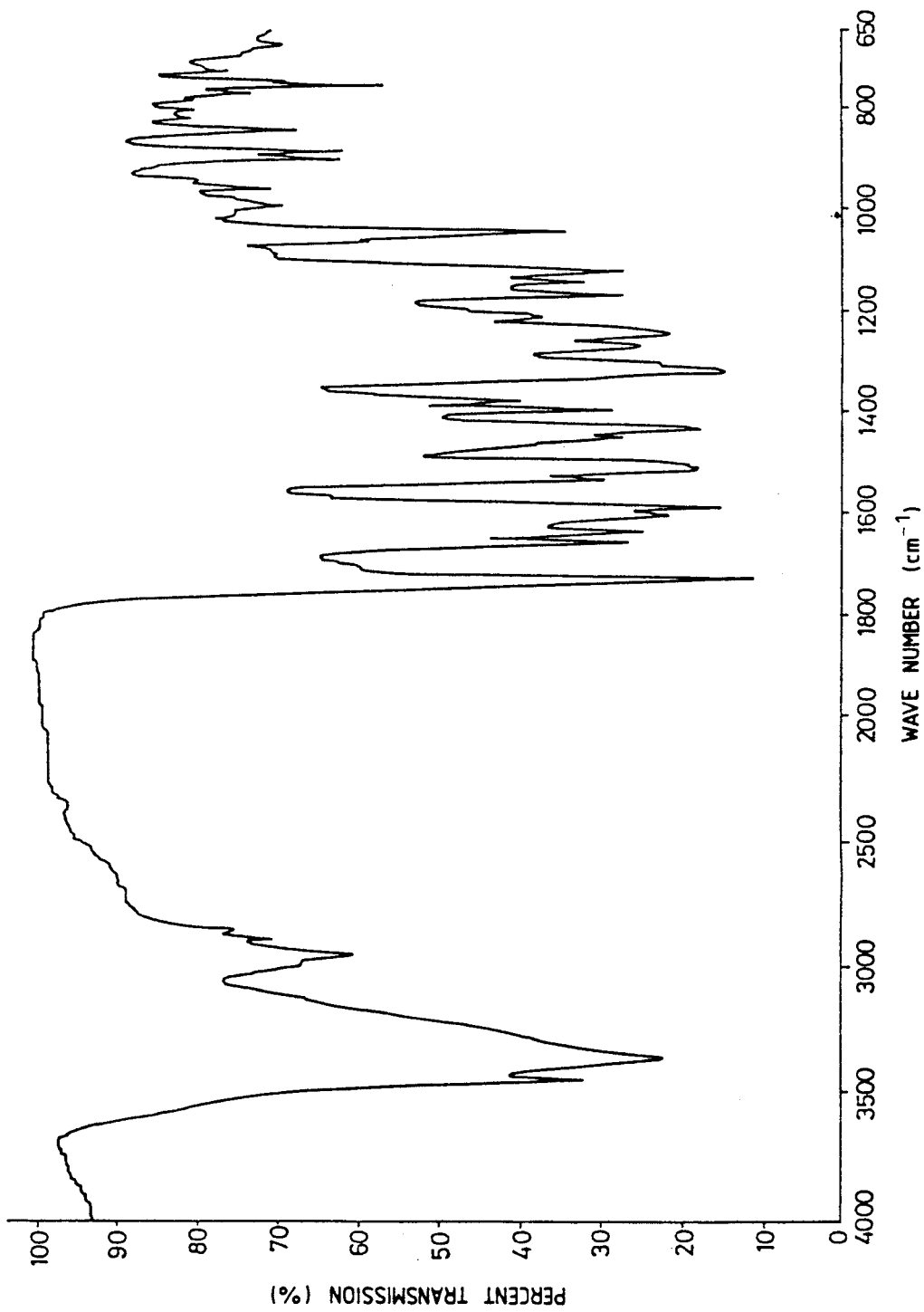
FIG. 10 shows an IR Spectrum of SF2582 C in a KBr tablet.

(8) IR Spectrum: as shown in FIG. 10

Figure 11:
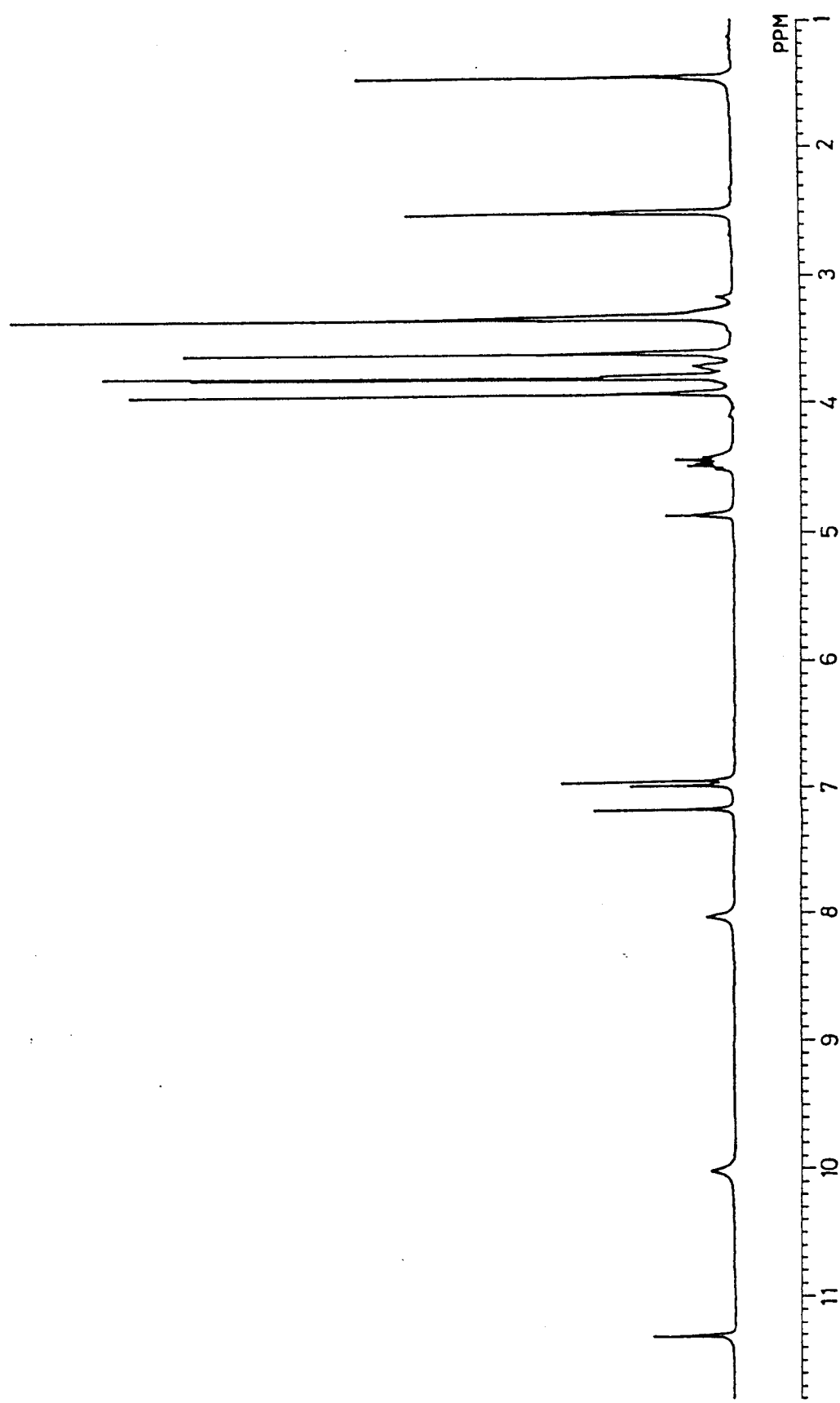
FIG. 11 shows a 1H NMR Spectrum (400 MHz) of SF2582 C in DMSO-d$_6$.

(9) $^1$H NMR Spectrum (400 MHz, DMSO-d$_6$): as shown in FIG. 11

Figure 12:
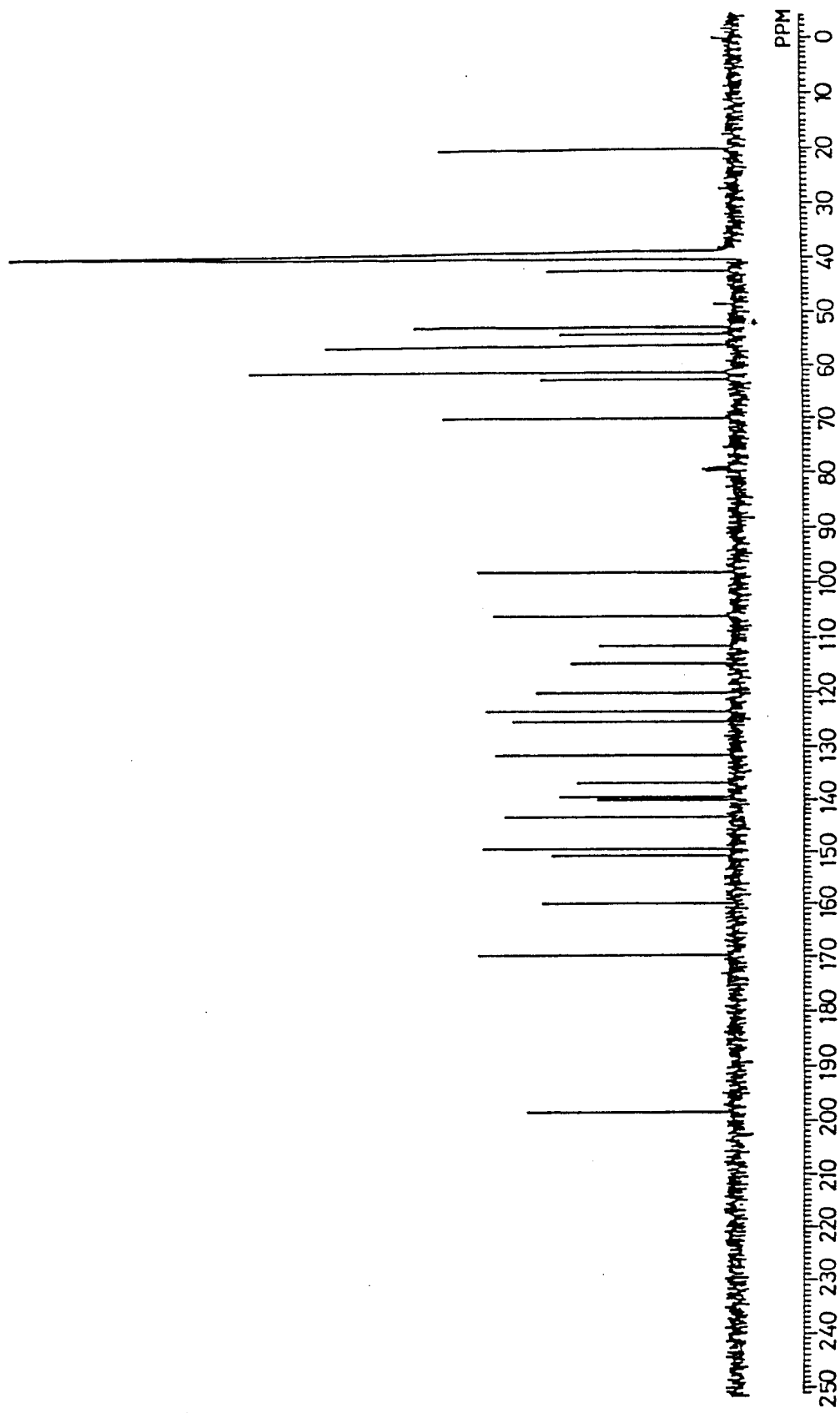
FIG. 12 shows a 13C NMR Spectrum (400 MHz) of SF2582 C in DMSO-d$_6$.

(10) $^{13}$C NMR Spectrum (100 MHz, DMSO-d$_6$): as shown in FIG. 12 δ(ppm): 198.1 (s), 169.5 (s), 159.6 (s), 150.5 (s), 149.3 (s), 143.1 (s), 139.9 (s), 139.2 (s), 136.5 (s), 131.4 (s), 125.3 (s), 123.4 (s), 120.0 (s), 114.5 (s), 111.4 (d), 105.9 (d), 98.2 (d), 70.1 (s), 62.6 (t), 61.3 (q), 61.1 (q), 56.1 (q), 54.1 (t), 52.8 (q), 42.5 (d), 20.3 (q)

(11) Solubility: easily soluble in pyridine or dimethyl sulfoxide; slightly soluble in methanol; sparingly soluble in chloroform, hexane, ethyl. acetate, or water

(12) Thin Layer Chromatography (on silica gel plates produced by E. Merck, Darmstadt):

| Developing Solvent | Rf |
| --- | --- |
| chloroform-methanol (10:1) | 0.38 |
| toluene-acetone (1:1) | 0.62 |

(13) Color Reaction: positive with 10% sulfuric acid reagent, Lemieux reagent, Greig-Leaback reagent, or molybdate-sulfuric acid reagent; negative with ninhydrin reagent The microorganisms capable of producing SF2582 A, B, and C include strain SF2582 isolated from the soil of Sagamihara City, Kanagawa, Japan.

Strain SF2582 has the following microbiological properties:

I. Morphology

Vegetative mycelia extend long and branch. Aerial mycelia grow on starch agar, oatmeal agar, sucrose nitrate agar, etc. with abundant spore formation. Branching of the aerial hyphae is simple and no whirl is found. Spore chain at the top of the aerial hyphae mostly have a closed spiral form. According to electron microscopical observation, spores have a cyclindrical form, a size of 0.7 to 0.9 × 1.0 to 1.4 μm, and a smooth surface, and usually about 20 spores are linked. Sporangia, motile spores or sclerotia are not observed.

II. Growth on Various Media

Growth of strain SF2582 on various media is shown in Table 1 below. The observations were made after culturing at 28° C. for 2 to 3 weeks. The color standards in the parentheses are in accordance with *Color Harmony Manual* of Container Corporation of America.

TABLE 1

| Medium | Growth (Color of Reverse Side) | Aerial Hyphae | Soluble Pigment |
| --- | --- | --- | --- |
| sucrose-nitrate agar | fair (colorless) | abundant, beige grown (3ig) | nil |
| glucose-asparagine agar | fair to good (grayish yellow) | fair, beige (3ge) | nil |
| glycerol-asparagine agar | faint (grayish yellow) | fair, grayish yellow (2gc) | nil |
| malic acid-calcium agar | fair (ivory) | poor, white to grayish white (2dc) | nil |
| starch agar | fair to good (grayish yellow) | fair to abundant, gray (2ih) | nil |
| oatmeal agar | fair to good (grayish grown yellow) | abundant, beige grown (3ig) | nil |
| yeast-malt agar | fair to good (pale grown) | poor to fair, grayish white (2dc) to gray (2ih) | nil |
| tyrosine agar | faint to fair (yellowish brown) | fair, beige (3ge) | pale purple |
| nutrient agar | faint (yellowish brown) | nil | nil |
| Bennett agar | fair to good (pale yellow) | poor, grayish white (2dc) | nil |

III. Physiological Properties:

(1) Growth Temperature: grown at 15° to 38° C., optimumly 26 to 30° C., on a yeast-malt agar medium
(2) Liquefaction of Gelatin: positive
(3) Hydrolysis of Starch: positive
(4) Reduction of Nitrate: negative
(5) Peptonization of Skimmed Milk: positive Coagulation of Skimmed Milk: negative
(6) NaCl tolerance: grown in 7% NaCl-containing media but not grown in 10% NaCl-containing media.
(7) (Formation of Melanin-like Pigment: negative IV. Utilization of Carbon Source (ISP No. 9 medium):

(1) D-Glucose, glycerol, D-xylose, L-arabinose, D-mannitol, D-fructose, myo-innositol, and L-rhamnose are utilized.
(2) Sucrose is not utilized.
(3) Utilization of raffinose is doubtful.

V. Cell Wall Composition

Analysis by the method of Backer et al., *Appl. Microbial.*, Vol. 13, 236 (1965) revealed that diaminopimelic acid in the cell wall composition is of LL form.

From the above properties, it is reasonable to consider that strain SF2582 belongs to the genus Streptomyces of actinomycetes. The inventors designated strain SF2582 as Streptomyces sp. SF2582. Strain SF2582 is deposited in Agency of Fermentation Research Institute, Japan under the deposit number FERM BP-2087 in accordance with Budapest treaty.

Strain SF2582 is liable to variation in properties as is the case of other actinomycetes. Therefore, microorganisms which can be used in the present invention include not only strain SF2582 per se but all other strains derived therefrom and capable of producing SF2582 A, B, or C, such as spontaneous or induced mutants, zygotes, and genetic recombinants originating from strain SF2582.

The strain is cultured in a medium containing nutrients utilizable by general microorganisms. Known nutrient sources conventionally employed for cultivation of actinomycetes can be used. Specific examples of the nutrient sources are carbon sources, e.g., glucose, maltose syrup, dextrin, starch, molasses, and animal and vegetable oils; and nitrogen sources, e.g., soybean flour, wheat germ, corn steep liquor, cotton seedmeal, meat extract, peptone, yeast extract, ammonium sulfate, sodium nitrate, and urea. If desired, the medium can contain inorganic salts capable of providing a sodium ion, a potassium ion, a calcium ion, a magnesium ion, a cobalt ion, a chlorine ion, a phosphate ion, a sulfate ion or other ions. Further, organic or inorganic substances effective to assist cell growth and to accelerate production of SF2582 A, B or C can be added to the medium appropriately.

The cultivation can be suitably effected under aerobic conditions, and most suitably by submerged aeration culture. A suitable cultivation temperature is from 26° to 30° C. and, in most cases, around 28° C. The production of SF2582 A, B, or C varies depending on the medium or cultivation conditions. Usually, the accumulation reaches the maximum in 2 to 7 days by shake culture or tank culture when the accumulated amount in the culture reaches the maximum, cultivation is ceased, and the desired substance is isolated from the culture and purified.

Isolation of SF2582 A, B or C from the culture can be carried out by usual means taking advantage of the properties of the desired substance, such as filtration, solvent extraction, adsorption or partition column chromatography, gel filtration, dialysis, precipitation, or the like technique, either alone or in combination thereof. For example, SF2582 A, B, and C can be extracted with acetone-water or methanol-water from the fungus body. The aqueous extract is then extracted with a water-immiscible organic solvent, e.g., butanol and ethyl acetate, thereby passing the active components into the organic layer. SF2582 A, B, and C can further be purified by column chromatography on an adsorbent, e.g., silica gel ("Wako Gel C-200" made by Wako Pure Chemical Inds., Ltd.) and alumina, Sephadex LH-20 (made by Pharmacia Co.), etc.

The derivatives of the above substance according to the present invention are represented by the following formula (I):

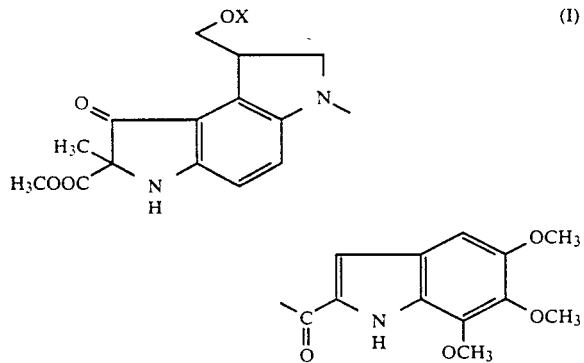

Wherein X and Y represents each an $RSO_2$-group, wherein R represents a p-tolyl, methyl or hydroxyl group, or a hydrogen atom, provided that X and Y do not represent hydrogen atoms at the same time.

A preferable example of $RSO_2$-group represented by X and Y is a methanesulfonyl group.

The compound of the formula (I) provided by the present invention may be produced by reacting SF2582 C with an esterifying agent such as sulfonic acid anhydride, sulfonyl halide, sulfuric acid anhydride/pyridine complex or chlorosulfonic acid in an inert solvent in the presence of a base to thereby esterify a hydroxyl group. Sulfonic acid anhydride and sulfonyl halide are preferably used as an esterifying agent. Examples of the inert solvent include benzene, toluene, tetrahydrofuran, dioxane, pyridine and N,N-dimethylformamide. Preferable inert solvents are tetrahydrofuran, pyridine and N,N-dimethylformamide. Examples of the base include alkylamines such as triethylamine and pyridine bases, preferably pyridine bases. The esterification would readily proceed at room temperature. In the case that a monoester is to be produced, however, it is preferable to carry out the above reaction at a temperature ranging from 20° to 25° C. for 1 to 4 hours with the use of an esterifying agent in a restricted amount, preferably 1 to 1.2 time by mol as much as the starting material, since the substance SF2582C carries two hydroxyl groups per molecule, as shown in the formula (C).

When the formula (I) is a monoester of the substance SF2582C, X represents a hydrogen atom and Y represents an $RSO_2$-group.

The present invention is now illustrated in greater detail by way of the following Examples and Test Examples, but it should be understood that the present invention is not deemed to be limited thereto.

EXAMPLE 1

A seed culture medium comprised 1.0% of starch, 1.0% of glucose, 1.0% of wheat germ, 1.0% of Pharmamedia, 0.2% of Staminol (produced by Sapporo Breweries Ltd.), 1.0% of soybean flour, 0.2% of sodium chloride, 0.2% of dipotassium hydrogenphosphate, and 0.05% of magnesium sulfate.

A production culture medium comprised 5.0% of starch maltose syrup, 0.5% of gluten meal, 1.0% of soybean flour, 0.5% of meat extract, 0.2% of Staminol, 0.1% of magnesium sulfate heptahydrate, 0.2% of sodium chloride, and 0.001% of cobalt chloride hexahydrate.

Before sterilization, the seed culture medium and the production culture medium were adjusted to a pH of 7.0 and 6.5, respectively.

A 100 ml-volume Erlenmeyer flask containing 20 ml of the seed medium was sterilized at 120° C. for 30 minutes, and the medium was inoculated with 2 to 3 (platinum) loopfuls of a slant agar culture of Streptomyces sp. SF2582 (FERM BP-2087) and shake-cultured at 28° C. for 3 days to prepare a first seed culture.

A 500 ml-volume Erlenmeyer flask containing 80 ml of the seed medium was sterilized at 120° C. for 30 minutes, and 2.4 ml of the above prepared first seed culture was inoculated thereon, followed by shake-culturing at 28° C. for 1 day to obtain a second seed culture.

A 5 l-volume Erlenmeyer flask containing 1 liter of the seed culture medium was sterilized at 120° C. for 30 minutes and inoculated with 30 ml of the second seed culture, followed by shake-culturing at 28° C. for 1 day to prepare a third seed culture.

Each of five tanks (300-l volume) each containing 200 l of the production medium having been sterilized at 120° C. for 30 minutes was inoculated with 2 l of the third seed culture and cultivated at 28° C. for 5 days under aeration (100 l/min) and shaking (100 rpm in the initial stage of cultivation; 130 rpm after 24 hours from the start of cultivation).

After completion of the cultivation, diatomaceous earth was added to the culture as a filtration aid, and the culture was filtered to recover a cake containing the cells.

EXAMPLE 2

The cake obtained in Example 1 was extracted with 350 l of a 60% acetone aqueous solution. The extract containing active components was concentrated under reduced pressure to a volume of 100 l, and the concentrate was extracted with 100 of ethyl acetate. The active component-containing extract was concentrated under reduced pressure to obtain 240 g of an oily substance. One liter of n-hexane was added thereto, and the hexane-soluble matter was removed. The hexane-insoluble matter was dried to obtain 102 g of an oily substance, which was then passed through a column packed with 3 l of silica gel (Wako Gel C-200), washed with 4 l of chloroform, and developed with 7 l of a mixed solvent of chloroform and methanol (50:1) to collect 500 ml fractions. Fraction Nos. 3 to 11 containing SF2582 A and B were combined and concentrated to obtain 16 g of an oily substance. The oily substance (16 g) was passed through a column of 800 ml of silica gel (Wako Gel C-200), washed successively with 1 l of benzene-acetone (20:1) and 2.5 l of benzene-acetone (10:1), and then developed with 2.5 l of a mixed developing solvent of benzene-acetone (5:1) to collected 30 ml fractions. Fraction Nos. 12 to 52 containing SF2582 A and B were combined and concentrated to dryness under reduced pressure to obtain 2.63 g of a crude yellowish brown powder.

The powder (2.63 g) was dissolved in a small amount of methanol, and the solution was passed through a column packed with 2.0 l of Sephadex LH-20 using methanol and developed with methanol to collect 30 ml fractions. Fraction Nos. 78 to 92 containing SF2582 B were combined and concentrated to dryness under reduced pressure to recover 208 mg of SF2582 B (purity about 50%). Fraction Nos. 95 to 124 containing SF2582 A were combined and concentrated to dryness under reduced pressure to recover 422 mg of SF2582 A (purity about 45%).

The crude powder of SF2582 A (422 mg) was subjected to preparative layer chromatography ("Art 5717" produced by E. Merck, Darmstadt) and developed with chloroform-methanol (20:1). A yellow band in the vicinity of Rf=0.6 was scraped off, extracted with ethyl acetate, followed by filtration. The filtrate was concentrated to dryness to obtain 256 mg of SF2582 A as an orange powder. then, the powder was dissolved in 12 ml of warm methanol. On standing at 5° C. for 1 day, there was precipitated SF2582 A, which was collected by filtration and dried to finally obtain 182 mg of SF2582 A as a yellowish orange powder.

Similarly, the crude powder of SF2582 B (208 mg) was subjected to preparative layer chromatography ("Art 5744" produced by E. Merck, Darmstadt) and developed with chloroform-methanol (20:1). A yellow band in the vicinity of Rf=0.6 was scraped off, extracted with ethyl acetate, and filtered. The filtrate was concentrate to dryness under reduced pressure to obtain 124 mg of SF2582 B. The product was again subjected to preparative layer chromatography using benzene-acetone (5:2) as a developing solvent to obtain 92 mg of SF2582 B. The resulting product (92 mg) was dissolved in a small amount of methanol, and the solution was passed through a column packed with 350 ml of "Toyopearl HW-40" (produced by Tosoh Corporation) using methanol and developed with methanol to collect 10 ml fractions. Yellowish orange fraction of from Nos. 46 to 54 containing SF2582 B were combined and concentrated to dryness to recover 88 mg of SF2582 B as a yellowish orange powder.

EXAMPLE 3

The cell cake obtained in Example 1 was extracted with 350 l of a 60% acetone aqueous solution. The extract containing the active components was concentrated under reduced pressure to obtain a 100 l of an aqueous solution, which was then extracted with 100 l of ethyl acetate. The ethyl acetate extract was concentrated under reduced pressure to obtain 222 g of an oily substance. To the oily substance was added 1 l of n-hexane, and the hexane-soluble matter was removed. The hexane-insoluble matter was dried to obtain 96 g of an oily substance. The product was passed through a column containing 3 l of silica gel (Wako Gel C-200), washed with 4 l of chloroform, and developed with a mixed solvent of chloroform-methanol (50:1) (10 l) to collect 500 ml fractions. Active fraction Nos. 12 to 16 containing SF2582 C were combined and concentrated to precipitate yellowish orange crystals, which were collected by filtration and dried to obtain 920 mg of crude crystals of SF2582 C. The resulting crude crystals (920 mg) were recrystallized twice from a mixed solvent of chloroform-methanol (5:1) to obtain 450 mg of SF2582 C as orange crystals.

EXAMPLE 4

Production of SF2582 C monomethanesulfonate (Compound 2) and SF2582 C dimethanesulfonate (Compound 1)

40 mg of SF2582 C as obtained in Example 3 was dissolved in 5 ml of anhydrous N,N-dimethylformamide and 0.1 ml of triethylamine and 50 mg of methanesulfonic anhydride were added thereto. The obtained mixture was allowed to react at 25° C. for ten minutes. The reaction mixture was extracted with 20 ml of benzene and 20 ml of water and the benzene phase was separated, washed with water and dried by adding anhydrous sodium sulfate thereto. After filtering off the sodium sulfate, the benzene solution was concentrated under reduced pressure. Thus, a yellow solid was obtained as the residue. This product was further purified by silica gel chromatography (solvent: benzene/ethyl acetate (1 : 1)) to thereby obtain the following three fractions.

Fraction 1: SF2582 C dimethanesulfonate (Compound 1)

yield: 41 mg.

$^1$H NMR (CDCl$_3$, ppm): 9.36 (s), 8.60 (s), 6.95 (d), 6.86 (s), 5.76 (s), 4.77 (dd), 4.65 (d), 4.48 (dd), 4.21 (m), 4.07 (s), 3.94 (s), 3.91 (s), 3.78 (s), 3.32 (s), 3.03 (s) and 1.70 (s). FD mass: 682 (M+1)$^+$.

Fraction 2: a mixture of Compounds 1 and 2 yield: 6.3 mg.

Fraction 3: SF2582 C monomethanesulfonate (Compound 2)

yield: 3.7 mg.

$^1$H NMR (CDCl$_3$, ppm): 9.73 (2), 8.60 (s), 6.95 (d), 6.83 (s), 5.73 (s), 4.59 (d), 4.07 (s), 4.01 (m), 3.93 (s), 3.91 (m), 3.90 (s), 3.87 (m), 3.77 (s), 3.31 (s) and 1.69 (s).

FD mass: 603 (M)$^+$.

EXAMPLE 5

Production of SF2582 C monotoluenesulfonate (Compound 3)

10 mg of SF2582 C was dissolved in 1.5 ml of anhydrous N,N-dimethylformamide and 0.2 ml of triethylamine and 10 mg of p-toluenesulfonyl chloride were added thereto. The obtained mixture was allowed to react at 25° C. for 30 minutes. The reaction mixture was extracted with 20 ml of benzene and 20 ml of water and the benzene phase was separated, washed with water and dried by adding anhydrous sodium sulfate thereto. Then the benzene solution was concentrated under reduced pressure. Thus a yellow solid was obtained as the residue. This product was further purified by silica gel chromatography (solvent: benzene/ethyl acetate (1 : 1)) to thereby give 12.6 mg of SF2582 C mono-p-toluenesulfonate.

$^1$H NMR (CDCl$_3$, ppm): 9.31 (s), 8.23 (s), 7.87 (d), 7.38 (d), 6.91 (d), 6.82 (s), 5.65 (s), 4.53 (m), 4.07 (s), 3.98 (s), 3.90 (s), 3.77 (s), 2.47 (s) an 1.64 (s).

FD mass: 679 (M)+·

EXAMPLE 6

Production of SF2582 C sulfate (Compound 4)

5 mg of SF2582 C was dissolved in 1 ml of anhydrous pyridine and 15 mg of a sulfuric anhydride/pyridine complex was added thereto. The obtained mixture was allowed to react at 25° C. for 18 hours. The reaction mixture was concentrated under reduced pressure and the residue thus obtained was purified by Sephadex LH-20 column chromatography (solvent: methanol/water (1:1)). Then a fraction showing an Rf value of 0.03 in silica gel TLC (mfd. by Merck Co., Inc., solvent: chloroform/methanol (9 : 1)) was collected. After removing the methanol under reduced pressure, the residue was lyophilized. Thus, 6 mg of SF2582 C sulfate (pyridine salt) was obtained.

SI mass: 606 $(M+1)^{30}$·

TEST EXAMPLE 1

Antimicrobial Activity of SF2582 A and B

The antimicrobial activity of SF2582 A and B on various test microorganisms shown in Table 2 below were determined by the serial dilution method on agar plate, and the minimum inhibitory concentrations (μg/ml) obtained are shown in Table 2 below.

TABLE 2

| Test Microorganism | Minimum Inhibitory Concn. (μg/ml) | |
|---|---|---|
| | SF2582 A | SF2582 B |
| Staphylococcus aureus 209P JC-1 | <0.025 | 0.05 |
| Staphylococcus aureus Smith S-424 | <0.025 | <0.025 |
| Staphylococcus aureus No. 26 | <0.025 | <0.025 |
| Staphylococcus epidermidis ATCC 14990 | 0.05 | 0.05 |
| Staphylococcus epidermidis 109 | <0.025 | 0.05 |
| Enterococcus faecalis ATCC 8043 | 0.05 | 0.10 |
| Bacillus anthracis No. 119 | 0.05 | 0.05 |
| Escherichia coli JC-2 | 12.5 | 25 |
| Escherichia coli No. 29 | 6.25 | 12.5 |
| Escherichia coli W 3630 RGN 823 | 6.25 | 12.5 |
| Escherichia coli JR 661 W/677 | 12.5 | 25 |
| Citrobacter freundii GN 346 | 3.13 | 6.25 |
| Salmonella typhi O-901-W | 3.13 | 3.13 |
| Salmonella enteritidis No. 11 | 0.78 | 1.56 |
| Salmonella typhimurium LT-2 | 12.5 | 25 |
| Salmonella sp. D-0001 | 12.5 | 25 |
| Shigella sonnei EW 33 Type 1 | 3.13 | 6.25 |
| Klebsiella pneumoniae PCI 602 | 25 | 50 |
| Klebsiella pneumoniae 22 #3038 | 25 | >100 |
| Proteus vulgaris OX 19 | >100 | 50 |
| Proteus mirabilis GN 310 | 25 | 25 |
| Providencia rettgeri J-0026 | 25 | 25 |
| Morganella morganii Kono | 50 | 50 |
| Serratia marcescens MB-3848 | 25 | 25 |
| Pseudomonas aeruginosa MB-3829 | 25 | 50 |
| Xanthomonas maltophilia M-0627 | 100 | 100 |

As can be seen from Table 2, the novel antibiotics of the present invention, SF2582 A and B, exhibit strong antimicrobial activities on various bacteria, particularly Gram positive bacteria.

TEST EXAMPLE 2

Antitumor Activity of SF2582 A and B

SF2582 A or B was intraperitoneally administered to mice in which P-388 tumor cells had been intraperitoneally implanted at a dose shown in Table 3, once a day for consecutive 2 days or only once, respectively. The effect of improving incidence of survival of animals (T/C %) is shown in Table 3 blow.

TABLE 3

| SF2582 A | | SF2582 B | |
|---|---|---|---|
| Dose (mg/kg) | T/C (%) | Dose (mg/kg) | T/C (%) |
| 2.14 | 80 | 10.0 | 80 |
| 0.54 | 128 | 2.5 | 159 |
| 0.13 | 148 | 0.63 | 159 |
| 0.033 | 114 | 0.16 | 117 |

It is apparent from Table 3 that SF2582 A and B exhibit strong antitumor activity on leukosarcoma P-388 in mice.

TEST EXAMPLE 3

Antitumor Activity of SF2582 C

Cytotoxicity of SF2582 C on various test tumor cells shown in Table 4 below was determined as follows. After SF2582 C was added to a medium, the test tumor cells were cultured at 37° C. for 72 hours in 5% $CO_2$. After the culturing, a 50% inhibitory concentration ($IC_{50}$) of SF2582 C on the cells was calculated by the probit method. The results obtained are shown in Table 4.

TABLE 4

| Tumor Cells | Origin | $IC_{50}$ (μg/ml) |
|---|---|---|
| P-388 | mouse leukemia | 9.4 |
| P-388/ADR | mouse leukemia resistant to multiple drugs | 14.5 |
| L-1210 | mouse leukemia | 1.3 |
| L-1210/CPR | mouse leukemia resistant to Cisplatin | 7.9 |
| Meth-A | mouse fibrosarcoma | 42.0 |
| B16 | mouse melanoma | 5.1 |
| K562 | human leukemia | 35.6 |
| PC10 | human lung cancer | 14.1 |
| PC13 | " | 39.5 |
| PC14 | " | >50.0 |
| HMV-1 | human melanoma | 12.1 |
| KB | human nasopharynx | 18.0 |
| HL-60 | human leukemia | 31.5 |

It can be seen from Table 4 that SF2582 C exhibits cytoxicity on various tumor cells.

TEXT EXAMPLE 4

Acute Toxicity of SF 2582 A, B, and C

SF2582 A or B was intraperitoneally administered to mice, and the animals were observed for 2 weeks. As a result, $LD_{50}$ of SF2582 A was 0.25 to 1.0 mg/kg and that of SF2582 B was 1.0 to 2.0 mg/kg. In the acute toxicity test of SF2582 C in mice, there was no case of death at a dose of 200 mg/kg (i.p.).

TEST EXAMPLE 5

Cytotoxic effect of Compounds 1 to 4 as obtained in Examples 4 to 6 were evaluated by incubating P-388 mouse leukemia cells at 37° C. for 72 hours in 5% $CO_2$ in the presence of each compound, and calculating a 50% growth inhibition concentration on P-388 cells. The results are shown in Table 5.

TABLE 5

| Compound No. | $IC_{50}$ (ng/ml) |
|---|---|
| 1 | 60 |
| 2 | 4 |
| 3 | 2500 |
| 4 | 1000 |

TABLE 5-continued

| Compound No. | IC$_{50}$ (ng/ml) |
| --- | --- |
| SF2582C (control) | 9400 |

TEST EXAMPLE 6

To evaluate antitumor activity of the test compounds, the following therapeutic test was conducted.

P-388 tumor cells were transplanted into the abdominal cavity of a mouse. A test compound was intraperitoneally administered to the animal once a day for two days. The effect thus observed is expressed in ILS (%).

$$ILS\ (\%) = \frac{\text{Average life-elongation (days) of test group}}{\text{Average survival time (days) of control group}} \times 100$$

The results are shown in Table 6.

TABLE 6

| Compound No. | Dose (mg/kg) | ILS (%) |
| --- | --- | --- |
| 1 | 21 | 54 |
| 1 | 7 | 40 |
| 1 | 2.4 | 40 |
| 2 | 1 | 40 |
| 2 | 0.5 | 40 |
| 2 | 0.25 | 15 |

Note:
Each group had five animals.

Tables 5 and 6 obviously indicate that the compounds of the present invention have each an intense antitumor activity. Thus, these compounds are expected as highly effective antitumor agents.

While the invention has been described in detail and with reference to specific embodiments thereof, it will be apparent to one skilled in the art that various changes and modifications can be made therein without departing from the spirit and scope thereof.

What is claimed is:

1. A compound represented by formula (I):

wherein X and Y each represent an RSO$_2$ group, wherein R represents a tolyl, methyl or hydroxyl group, or a hydrogen atom, provided that X and Y do not represent hydrogen atoms at the same time; and 2. The compound according to claim 1, wherein Y represents a methanesulfonyl group.

3. The Compound according to claim 1, wherein X represents a hydrogen atom.

4. The Compound according to claim 1, wherein X and Y both represent a methanesulfonyl group.

* * * * *